(12) United States Patent
Ponce et al.

(10) Patent No.: US 7,651,862 B2
(45) Date of Patent: Jan. 26, 2010

(54) METHOD AND APPARATUS FOR DISTRIBUTED SENSING OF VOLATILES USING A LONG PERIOD FIBER GRATING SENSOR WITH MODULATED PLASTIC COATING FOR ENVIRONMENTAL MONITORING

(75) Inventors: Adrian Ponce, Altadena, CA (US); Dmitri A. Kossakovski, Pasadena, CA (US); Gregory H. Bearman, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1033 days.

(21) Appl. No.: 10/469,216

(22) PCT Filed: Feb. 26, 2002

(86) PCT No.: PCT/US02/05816

§ 371 (c)(1),
(2), (4) Date: Jan. 28, 2004

(87) PCT Pub. No.: WO02/068936

PCT Pub. Date: Sep. 6, 2002

(65) Prior Publication Data

US 2004/0115824 A1 Jun. 17, 2004

Related U.S. Application Data

(60) Provisional application No. 60/271,667, filed on Feb. 26, 2001.

(51) Int. Cl.
*G01N 21/17* (2006.01)
*G01N 21/84* (2006.01)
*G02B 6/10* (2006.01)

(52) U.S. Cl. .............. 436/164; 250/227.16; 385/12; 385/13; 422/82.05; 422/82.09; 422/82.11

(58) Field of Classification Search ............ 250/227.16; 385/12–13; 422/82.05, 82.09, 82.11; 436/164
See application file for complete search history.

(56) References Cited

U.S. PATENT DOCUMENTS 5,015,843 A * 5/1991 Seitz et al. ............. 250/227.21

(Continued)

FOREIGN PATENT DOCUMENTS

DE 19530985 * 8/1995

(Continued)

OTHER PUBLICATIONS

Michie, W. C. et al, Optics Letters 1995, 20, 103-105.*

(Continued)

*Primary Examiner*—Arlen Soderquist
(74) *Attorney, Agent, or Firm*—Daniel L. Dawes; Marcus C. Dawes

(57) ABSTRACT

Optical time domain reflectometry caused by absorption of a volatile or analyte into the fiber optic cladding is used an optical nose. The fiber optics (14) are covered with a gas permeable film (44) which is patterned to leave millimeter wide gas permeable notches (48a-48d). The notches contain a sensing polymer that responds to different gases by expanding or contracting.

11 Claims, 2 Drawing Sheets

U.S. PATENT DOCUMENTS

| | | | | |
|---|---|---|---|---|
| 5,144,690 | A | * | 9/1992 | Domash ................. 385/12 |
| 5,378,889 | A | * | 1/1995 | Lawrence ............ 250/227.16 |
| 5,430,815 | A | * | 7/1995 | Shen et al. ................. 385/13 |
| 5,744,794 | A | * | 4/1998 | Michie et al. ......... 250/227.16 |
| 5,982,959 | A | * | 11/1999 | Hopenfeld ................. 385/12 |

FOREIGN PATENT DOCUMENTS

| | | | |
|---|---|---|---|
| JP | 61-260204 | * | 11/1986 |
| JP | 63-266340 | * | 11/1988 |
| JP | 64-1934 | * | 1/1989 |

OTHER PUBLICATIONS

Michie, W. C. et al, SPIE 1994, 2360, 130-133.*
Bownass, D. C. et al, Optics Letters 1997, 22, 346-348.*
MacLean, A. et al, SPIE 1998, 3330, 134-144.*
Muto, S. et al, SPIE 1998, 3417, 61-69.*
Gusmeroli, V. et al, Optics Letters 1989, 14, 1330-1332.*
Shlyagin, M. G. et al, SPIE 2000, 4074, 108-115.*

* cited by examiner

METHOD AND APPARATUS FOR DISTRIBUTED SENSING OF VOLATILES USING A LONG PERIOD FIBER GRATING SENSOR WITH MODULATED PLASTIC COATING FOR ENVIRONMENTAL MONITORING

RELATED APPLICATIONS

This application is a national phase filing under 35 USC 371 of PCT Patent Application Ser. No. PCT/US02/05816, filed on Feb. 26, 2002 which claims the benefit under 35 USC 120 claims the benefit of the filing date of U.S. Provisional Patent Application 60/271,667, filed on Feb. 26, 2001.

The invention described herein was made in performance of work under a NASA contract and is subject to the provisions of Public Law 96-517 (35 USC 202) in which the Contractor has elected to retain title.

BACKGROUND OF THE INVENTION

1. Field of the Invention

The invention is in the field of optical time domain reflectometry and in particular the use of optical time domain reflectometry for sensing and quantifying volatiles.

2. Description of the Prior Art

A major goal of analyte detection research is to develop inexpensive, fast, reliable, and sensitive detectors. Unfortunately, the technologies developed to date have only met some of these goals, and no single device has sufficiently attained a majority of them.

Classical detection methods such as liquid chromatography (LC), gas chromatography (GC), and supercritical fluid chromatography (SFC), in combination with mass spectrometry, are widely used and provide accurate identification of analytes and quantitative data. However, these techniques are time consuming, extremely expensive, require sample preconcentration, and are difficult or impossible to adapt to field use.

Biosensors (i.e., devices containing biological material linked to a transducing apparatus) have been developed to overcome some of the shortcomings of the classical analyte detection techniques. Many currently used biosensors are associated with transducer devices that use photometry, fluorimetry, and chemiluminescence; fiber optics and direct optical sensing (e.g., grating coupler); surface plasmon resonance; potentiometric and amperometric electrodes; field effect transistors; piezoelectric sensing; and surface acoustic wave. However, there are major drawbacks to these devices, including their dependence on a transducing device, which prevents miniaturization and requires a power source. These disadvantages make such devices too complex, expensive, or unmanageable for many routine analyte detection applications such as field work or home use. Additionally, many of these devices are limited by the lack of stability and availability of the biological materials (e.g., proteins, antibodies, cells, and organelles).

Immunoassay methods are also used for detecting certain types of analytes. In these methods, antibodies are developed to specifically bind to a target of interest (e.g., an analyte). By labeling the antibody (e.g., with dye or fluorescent or radioactive material), binding of the antibody to an analyte can be detected. However, immunoassay methods are limited in that they require production of antibodies against each analyte of interest. Antibodies cannot be generated against some types of analytes and their generation can be time consuming and expensive.

The art remains in need of analyte detectors that provide the specificity of biosensors but also provide the cost-efficiency, stability, accuracy, reliability, reproducibility, and robustness that is lacking from available technologies. In particular, development of devices that can be miniaturized with controlled shapes and that do not rely on an energy source would also be very beneficial, particularly for routine field work and home use.

The electronic nose is the current state-of-the art technology for gas-phase chemical sensing. It consists of an array of carbon-black polymer composite films that act as vapor sensing elements by exhibiting a resistance response to vapor. The response across the array can be analyzed using chemometric methods that yield diagnostic patterns, which allow classification and quantification of analytes in gas-phase mixtures.

What is needed is some kind of volatile detection means which overcomes each of the limitations of the prior art.

BRIEF SUMMARY OF THE INVENTION

The invention presents a new strategy for gas-phase chemical sensing based on optical time domain reflectometry (OTDR). OTDR enables fast and analytical measurements of vapor mixtures along kilometers of optical fiber. Unlike electronic noses, which have a single point sensor, the optical nose disclosed below is a true distributed sensor, with a large number of closely spaced sensing points along the length of the optical fiber. In addition, the optical nose can be employed in areas where electromagnetic interference renders an electronic nose ineffective. Finally, the polymers used in the OTDR sensing scheme do not require doping with carbon-black, thus reducing fabrication complexity.

The optical nose of the invention permits distributed environmental monitoring of volatile chemicals in the atmosphere. As a true distributed sensor it utilizes a sensing element that can monitor a large area with good spatial resolution.

Distributed environmental monitoring of volatile chemicals in the atmosphere can be accomplished by using optical fibers as sensing elements and picosecond laser pulses to locate the response of the fiber to volatiles. A change in gas-phase concentration is transduced to an optical response by choosing a polymer coating for an optical fiber that swells upon absorbing volatile substances. Thus, as the coating absorbs volatiles and swells, the resulting stress triggers a change in refractive index that partially reflects the picosecond pulse launched at the beginning of the fiber. The location of the swelling is found by measuring the time-of-flight for the picosecond pulse (OTDR technique).

In another embodiment of the invention, a swelling polymer coating is deposited on the fiber in a periodic manner in or with a non-swelling polymer coating. The periodicity of the pattern of polymer coating is chosen to produce a long period grating with desired optical characteristics in fiber core surrounded by conventional cladding. When the fiber is exposed to volatile components, the polymer stripes swell thereby inducing periodic stress on the fiber cladding and core leading to a periodic pattern of stressed regions in core. The periodic pattern of stress changes the coupling of forward propagating modes of light in the fiber. Attenuation of specific wavelengths is dependent on the degree of strain, and so the fiber is sensitive to the concentration of analyte causing the swelling.

Thus the invention is defined as a method of analyzing an analyte dispersed in a medium comprising the steps of providing an optic fiber with at least one analyte-sensitive sensitive material disposed thereon, the analyte-sensitive material inducing a stress on the optic fiber; and sensing the stress induced on the optic fiber to identify exposure of the analyte-sensitive material to the analyte. The expanding or contracting polymer is disposed on the exterior of a conventional optic fiber. In one embodiment the polymer is disposed in a notch defined into the optic fiber to induce a bend in the optic fiber on exposure to the analyte. In another embodiment the polymer comprises a sequence of periodic longitudinal depositions of the expanding or contracting polymer on the fiber to create a periodic stress-induced grating in the optic fiber.

In one embodiment the plurality of analyte-sensitive materials are disposed at predetermined longitudinal positions on the optic fiber, and the step of sensing the stress induced on the optic fiber comprises performing optical time domain reflectometry to determine the longitudinal position of the analyte-sensitive material on the optic fiber.

In another embodiment, the step of sensing the stress induced on the optic fiber comprises sensing attenuation of light at a predetermined wavelength in the periodic stress-induced grating in the optic fiber.

The method further comprises the step of determining the concentration of the analyte by the degree of stress induced on the optic fiber, namely the step of determining the intensity of a reflected light pulse from a stress-induced bending of an optic fiber, or the step of determining the intensity of a attenuated light from a stress-induced grating in an optic fiber.

A plurality of optic fibers each with a plurality of analyte-sensitive materials disposed thereon can be provided so that the plurality of optic fibers form an array of sensing points. Each sensing point has a differential response to an analyte. In this embodiment the step of sensing the array of sensing points is followed by the step of analyzing the array to form a pattern recognition of the analyte.

The invention is also defined as an apparatus for analyzing an analyte dispersed in a medium according to the above methodologies.

Still further, the invention includes an optic fiber comprising a fiber core, cladding, and a periodic coating of polymer disposed on or in the cladding. The periodic coating is arranged and configured with respect to the core and cladding to apply a stress on the core when an analyte interacts with the polymer to swell or contract the polymer.

In one embodiment the periodic coating is comprised of an uniform coating of polymer disposed on the cladding and a patterned film is disposed onto the polymer coating to selectively expose asymmetric sections of the polymer coating. These asymmetric sections cause a bending force to be applied the cladding and core when the exposed polymer coating swells or contracts. In particular the periodic coating is comprised of a nonexpanding or noncontracting uniform coating on the cladding with notches defined in the nonexpanding uniform coating, and expanding or contracting polymer disposed in the notches.

In yet another embodiment, the periodic coating is comprised of a sequence of expanding or contracting rings of polymer separated by rings of nonexpanding or noncontracting rings of polymer so that a stress-induce optical grating is induced in the core and cladding.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 4a is side cross-sectional view of the fiber when it is unexposed to a volatile and before any stress induced periodicity is imposed on the core and cladding of the optic fiber. FIG. 4b is side cross-sectional view of the fiber after it is exposed to a volatile and after a stress induced periodicity is imposed on the core and cladding of the optic fiber.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Fiber optics are used to detect a change in optical time domain reflectometry (upon) absorption of an analyte onto the fiber optic cladding. The fiber optics are covered with a gas permeable film which is patterned to leave millimeter wide gas permeable notches. The notches contain a sensing polymer that responds to different gases by expanding or contracting. This asymmetric swelling or contraction of the polymer causes a change in the refraction in the fiber optic cable and OTDR is then used to localize the source of the volatile. The sensors can be arrayed to give a characteristic response for each volatile, so that its identity and amount is determined. The use of a reference fiber is included to account for temperature variations. In another embodiment a longitudinal periodic array of swelling and nonswelling polymer coatings on the optic fiber create a stress-induced long period periodic grating in the core of the fiber. The stress dependent attenuation of the long period periodic grating in the core is then used as a detecting mechanism for the volatile. Although in the following the polymer will typically be referenced as a swelling or nonswelling polymer, it is to be expressly understood that in this specification the term "swelling or nonswelling polymer" includes within its meaning both expanding and/or contracting materials in the term "swelling polymer" and nonexpanding and/or noncontracting materials in the term "nonswelling polymer." While expanding materials are preferred, all that is required is that the material in question induce a stress on the core of the optic fiber with which it is associated.

Figure 1:
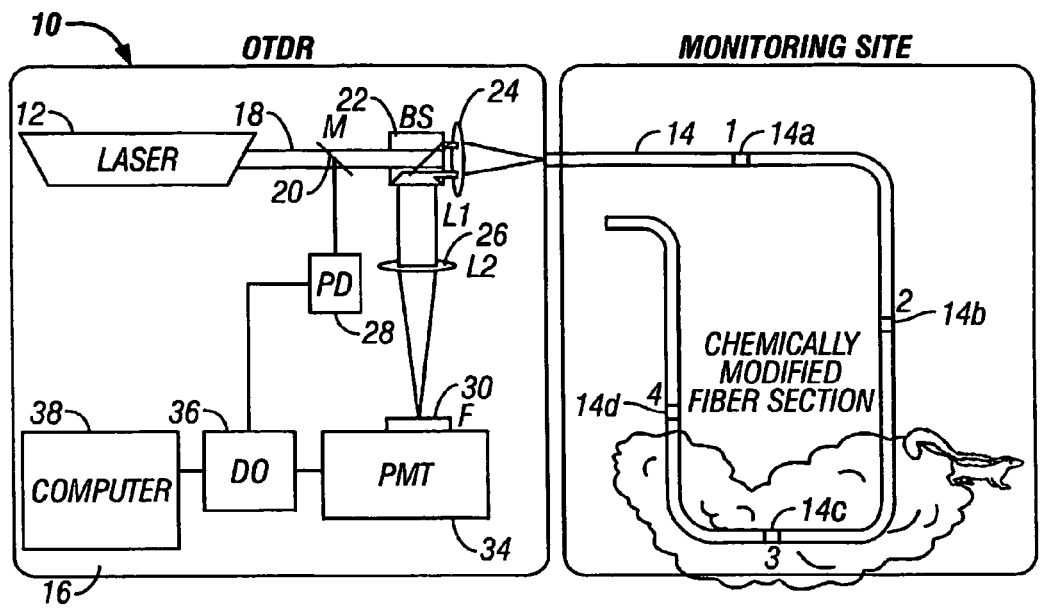
FIG. 1 is a diagrammatic depiction of an optical nose using a fiber sensing array devised according to the invention.

The optical nose 10 of the invention diagrammatically shown in FIG. 1 is based on the principles of optical time domain reflectometry (hereinafter OTDR), in which a short, typically a picosecond laser pulse from a laser 12 is launched into a fiber optic 14. The picosecond pulse in beam 18 from laser 12 is partially reflected from mirror 20 into digital oscilloscope 36 to set the timing mark or reference for time zero. The pulse continues through beam splitter 22 into optics 24 where it is inserted into fiber optic 14. The pulse travels down fiber 14 and is reflect back in fiber 14 by one or more sensor points 14a-14d described below depending on whether an analyte for which sensor points 14a-14d are sensitized is present in the environment or not. The degree or intensity of the reflection of the light pulse is a function of the concentration of the analyte. The reflected pulse, if any, returns along fiber 14 to optics 24 and is reflected by beam splitter 22 into a sensor, which in the illustrated embodiment includes a lens or optics 26, filter 30 and a photomultiplier tube 34. The output of photomultiplier tube 34 is also coupled to digital oscilloscope 36 and provides the reflected signals from sensor points 14a-14d.

Figure 2:
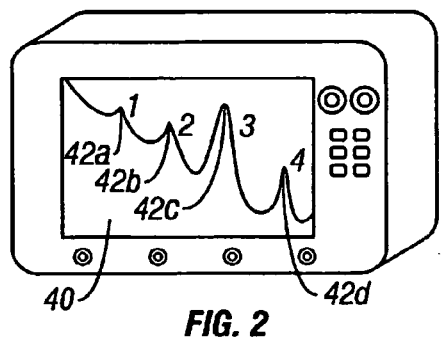
FIG. 2 is a CRT screen display of the output of the optical nose of FIG. 1.

The data is processed for nonlinearity and other data corrections, if needed, by computer or logic circuit 38 and displayed on a CRT screen 40 shown in FIG. 2. The graph on screen 40 in FIG. 2 diagrammatically depicts four reflected signals 42a-42d, one from each of the sensor points 14a-14d in or on fiber 14 discussed below. The time delay of a reflected pulse from each of the sensor points 14a-14d of fiber 14 is unique and is determined by the known speed of light in fiber 14. The optical nose 10 of FIG. 1 has been shown only for illustrative purposes and it is to be expressly understood that many other photonic circuits can be employed to perform the necessary optical time domain reflectometry other than the one illustrated. OTDR equipment is conventional and is available in manner forms as ready-made analytic instruments, all forms of which are expressly included within the teachings of the invention.

As stated above a fraction of the pulsed light is reflected back along fiber optic 14 to the OTDR source 16 due to microscopic variations of the refractive index along the fiber 14. Significant variations in refractive index are induced by shear stress from small radius microbending in fiber 14. Thus, by monitoring the intensity 42a-42d of the reflected light pulses as a function of time we can determine the location from the round trip time of the light and magnitude of shear stress at uniquely identified sensor points 14a-14d from the intensity of the reflected light. The optical nose 10 uses a fiber coating 44 on a optic fiber core 46 as shown diagrammatically in FIG. 3, which is comprised of polymers that absorb volatiles. The absorption of the volatile by the polymer leads to swelling and subsequent shear stress on the fiber, which causes the reflection of the light pulse. Thus, a change in concentration of volatiles is transduced into an optical signal that can be spatially localized along kilometers of optical fiber 14 using commercially available OTDR technology. The existence of volatile-sensitive polymers which swell in response to selected volatiles is well known. The choice of polymer-volatile pairs is extensive so that virtually any volatile or class of volatiles can be selectively sensed by a corresponding choice of polymer according to well known design choice in a manner consistent with the teachings of the invention.

Figure 3:
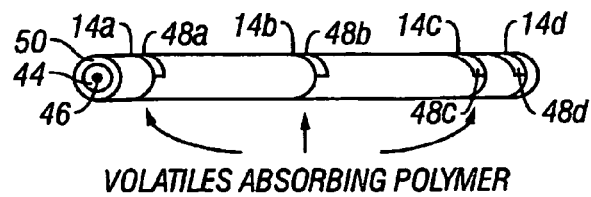
FIG. 3 is a diagrammatic depiction of a section of fiber optic provided with a plurality of sensor points comprised of semicircular notches filled with swelling polymer to bend the optic fiber.

In order to optimize the sensitivity of the optical nose 10, several embodiments that maximize the shear stress on the fiber 14 upon vapor absorption are envisioned. The simplest embodiment for mass manufacture is drawing optical fiber 14 with the entire polymer coating 44 comprised of the sensing polymer. The fiber 14 is then treated with a gas impermeable film 50, which is patterned to leave millimeter wide gas permeable notches 48a-48d that span half the circumference of the fiber 14 as shown in FIG. 3 and comprise sensor points 14a-14d. Consequently, the coating 44 in the notch 48a-48d will swell, while the coating 44 that is covered with the film 50 will not. Thus, asymmetric swelling of the coating 44 around the notches 48a-48d will induce greater shear stress than if the notches 48a-48d were to encompass the entire fiber circumference. The mechanical mechanism of bending caused by differential swelling is similar to the one that living plants use to bend their leaves toward the sun.

An alternative embodiment allows utilization of commercially available fibers. In this embodiment, the film 50 is removed in notches 48a-48d in the pattern stated above and replaced with the sensing polymer coating 44, which is painted onto the fiber 14. In both embodiments, temperature dependence effects can easily be accounted for by simply covering the entire surface of a control fiber (not shown) with a gas impermeable film. Thus, although only one fiber 14 has been shown in FIG. 1, it is to be understood that a multiplicity of fibers 14 can be coupled to optical nose 10 in parallel to provide for a spectrum of analyte detectors as well as a temperature or other control by which the output data may be normalized by computer 38 to a standardized test condition.

The specificity for determining the concentration of a constituent in a volatile chemical mixture is enabled in the invention by a concept similar to the one proposed for mammalian olfaction. In other words, an array of sensors or fibers and sensor points 14a-14d, which array has a differential response to chemicals across the array, provides a characteristic response. The elements of such an array contains maximal chemical diversity to maximize the cross section of analytes that can be characterized. Thus, a distinct response pattern is produced over the collection of sensors in the array to provide a 'fingerprint' that allows identification of the analyte in computer 38. Principal component analysis for dimensionality reduction of the data and application a neural-network or Bayes classifier for a pattern-recognition algorithm enables automated data analysis. Many other data reduction and analysis methodologies may be equivalently employed without departing from the scope of the invention.

In summary, the optical nose 10 described above enables true distributed sensing and quantification of chemical components in a mixture of volatile substances. OTDR instruments are commercially available and the disclosed modification of optical fibers can be readily implemented by methodologies which are also conventional.

Figure 4A:
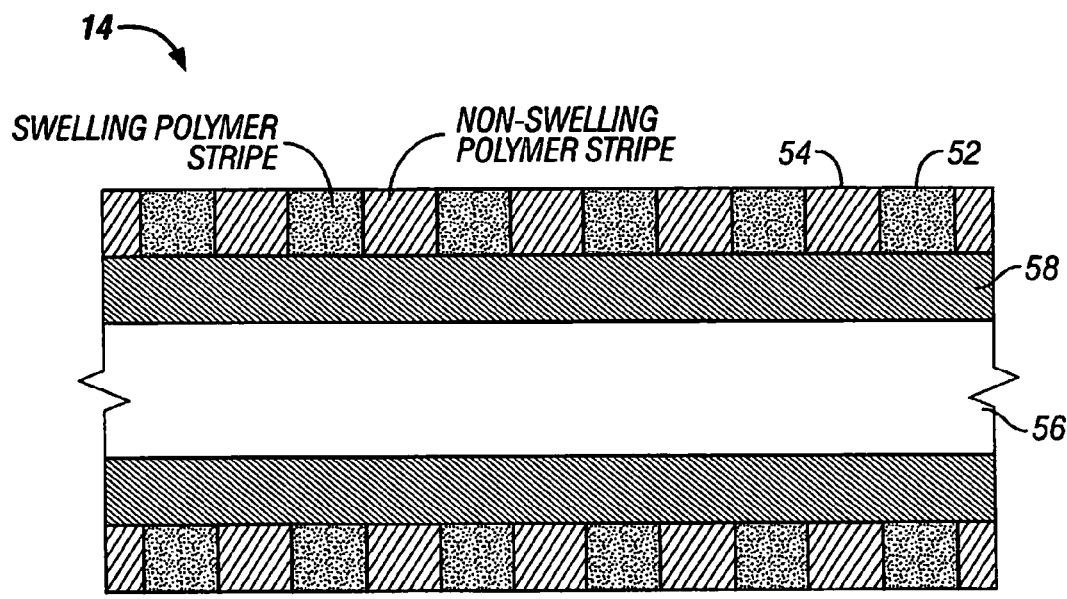
FIGS. 4a and 4b are side cross-sectional views of long period fiber grating using a periodic sequence of rings of swelling polymers and nonswelling polymers to create a stress induced grating in a conventional optic fiber.
Figure 4B:
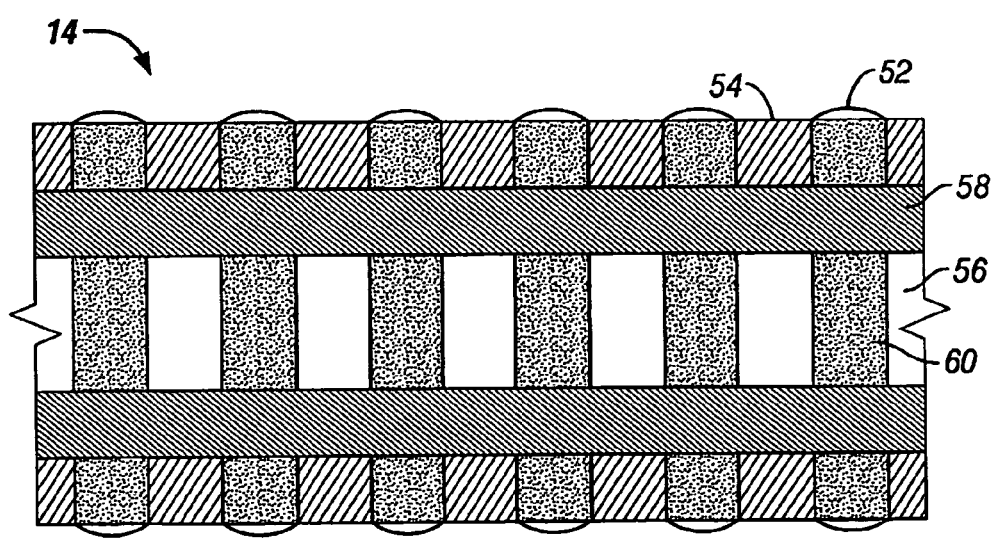

In another embodiment, an optical fiber 14 is used for environmental sensing has a specific structure which increases the sensitivity of the optical nose 10 described above. The swelling polymer coating 44 is arranged on the fiber 14 in a special periodic way to form a long period grating as shown in FIGS. 4a and 4b. Hence, the optic fiber 14 is called the "Tiger-Fiber" since it has a striped appearance. Since the degree of swelling in coating 44 can be low, the chemical sensitivity of fiber 14 in FIG. 3 can be limited.

Typical long period fiber gratings (LPFG) are photo-induced fiber devices which have periodic modulation of fiber core refraction index. The grating produces attenuation of one of more specific wavelengths in a single mode fiber. Strain, temperature and chemical environment sensors based on this LPFG structure are well known. The pitch of the gratings varies from tens to hundreds of micrometers depending on design objectives.

In the invention instead of permanently inducing the grating in a core of a specialized photosensitive fiber, a conventional optic fiber 14 is used. However, the plastic coating of the fiber 14 is prepared in a special way in the invention as described below. This coating represents a grating of alternating polymers 52, 54, swelling and non-swelling upon exposure to specific volatile analyte. The periodicity of the coating is determined by the desired optical characteristics of the LPFG grating according to well known design principles.

Without analyte present, the Tiger Fiber 14 of the invention in FIG. 4a transmits light without attenuation. Upon exposure to analyte, the chemically sensitive stripes 52 swell and induce periodic mechanical strain on the fiber 14, thereby configuring the fiber into an LPFG. This grating attenuates the transmission of specific wavelengths according to the grating design. The degree of the attenuation is related to the concentration of the analyte.

Tiger-Fiber 14 of FIGS. 4a and 4b is an improvement for the chemical sensitivity of the optical nose 10, because swelling of the coating is transduced into the attenuation of light by an LPFG, which is a stronger or more sensitive optical effect than just the bare change of local reflectivity utilized by optical nose 10 described above.

According to the invention a swelling polymer coating 52 is deposited on the fiber 14 in a periodic manner in a non-swelling polymer coating 54 as shown in the side cross-sectional view of FIG. 4a as opposed to single polymer patches or continuous intervals described above. Polymer coating 52 thus forms a sequence of circumferential rings of swelling polymer separated by an interleaved sequence of circumferential rings of nonswelling polymer 54 on the exterior of fiber 14 like beads on a tightly packed string necklace. The periodicity of the pattern of polymer coating 52 is chosen to produce a long period grating with desired optical characteristics in fiber core 56 surrounded by conventional cladding 58.

When the fiber 14 is exposed to volatile components, the polymer stripes 52 swell thereby inducing periodic stress on the fiber cladding 58 and core 56 leading to a periodic pattern of stressed regions 60 in core 56 as diagrammatically shown in FIG. 4b. Such a periodic pattern of stress changes the coupling of forward propagating modes of light in the fiber 14. Attenuation of specific wavelengths is dependent on the degree of strain, and so the fiber 14 is sensitive to the concentration of analyte causing the swelling. In this embodiment, the output signal is then not a reflected pulse, but the attenuation of a forward light beam, which may be pulsed or continuous. A computer or other data circuit is then used to read an attenuation spectrum or to sense the degree of attenuation from an array of LPFG fibers 14, each with a specific polymer grating, extending into the environment and looping back from a light source back to a light detector.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method of analyzing an analyte dispersed in a medium comprising:

providing an optic fiber with at least one analyte-sensitive material in the form of a swelling or contracting sensing polymer coating circumferentially surrounding the optic fiber, which coating is distributed as a longitudinal sequence of active circumferential stripes along the entire length of the optic fiber;

exposing the coated optic fiber to the medium to induce a stress along the optic fiber; and sensing the stress induced on the optic fiber to identify exposure of the analyte-sensitive material to the analyte, where the optic fiber has a cladding and where providing the swelling or contracting sensing polymer on the exterior of a optic fiber comprises embedding the swelling or contracting sensing polymer into a plurality of semicircular notches defined into a uniform polymer coating on the exterior of the cladding of the optic fiber; and inducing a plurality of bends in the optic fiber on exposure to the analyte to create a stress in the optic fiber to alter its optical property.

2. A method of analyzing an analyte dispersed in a medium comprising:

providing an optic fiber with at least one analyte-sensitive material in the form of a swelling or contracting sensing polymer coating circumferentially surrounding the optic fiber, which coating is distributed as a longitudinal sequence of active circumferential stripes alternated with a longitudinal sequence of inactive circumferential stripes along the length of the optic fiber to create a periodic stress-induced distributed grating in the optic fiber;

exposing the coated optic fiber to the medium to induce a stress along the distributed grating; and sensing the stress induced on the optic fiber to identify exposure of the analyte-sensitive material to the analyte.

3. The method of claim 2 where providing an optic fiber with at least one analyte-sensitive material to create the stress-induced distributed grating comprises providing the swelling or contracting sensing polymer on the exterior of a optic fiber by fully circumferentially surrounding the optic fiber with a plurality of uniform sensing polymer stripes.

4. A method of analyzing an analyte dispersed in a medium comprising:
   providing an optic fiber with at least one analyte-sensitive material in the form of a swelling or contracting sensing polymer coating circumferentially surrounding the optic fiber, which coating is distributed as a longitudinal sequence of active portions along the entire length of the optic fiber to create a stress-induced distributed grating in the optic fiber;
   exposing the coated optic fiber to the medium to induce a stress along the distributed grating; and
   optically sensing the stress induced on the optic fiber to identify exposure of the analyte-sensitive material to the analyte by means of the longitudinal sequence of active portions of the polymer, which active portions are embedded in a non-sensing polymer coating surrounding the fiber to identify exposure of the analyte-sensitive material to the analyte and sensing attenuation of light at a predetermined wavelength in the periodic stress-induced grating in the optic fiber.

5. An apparatus for analyzing an analyte dispersed in a medium comprising:
   an optic fiber with at least one analyte-sensitive material in the form of a swelling or contracting polymer coating circumferentially surrounding the optic fiber, which coating is distributed as a longitudinal sequence of active circumferential stripes alternated with a longitudinal sequence of inactive circumferential stripes along the length of the optic fiber to create a distributed periodic stress-induced grating in the optic fiber, the analyte-sensitive material inducing a stress on the optic fiber; and
   means for sensing the stress induced on the optic fiber to identify exposure of the analyte-sensitive material to the analyte.

6. An apparatus for analyzing an analyte dispersed in a medium comprising:
   an optic fiber with at least one analyte-sensitive material in the form of a swelling or contracting polymer coating circumferentially surrounding the optic fiber, which coating is distributed as a longitudinal sequence of active circumferential stripes along entire length of the optic fiber to create a distributed periodic stress-induced grating in the optic fiber, the analyte-sensitive material inducing a stress on the optic fiber; and
   means for sensing the stress induced on the optic fiber to identify exposure of the analyte-sensitive material to the analyte,
   where the distributed stress-induced grating in the optic fiber comprises a plurality of fully circumferentially surrounding uniform swelling or contracting polymer stripes embedded in a nonsensing coating.

7. An apparatus for analyzing an analyte dispersed in a medium comprising:
   an optic fiber with at least one analyte-sensitive material in the form of a swelling or contracting polymer coating circumferentially surrounding the optic fiber, which coating is distributed as a longitudinal sequence of active circumferential stripes along entire length of the optic fiber, the analyte-sensitive material inducing a stress on the optic fiber; and
   means for sensing the stress induced on the optic fiber to identify exposure of the analyte-sensitive material to the analyte,
   where the optic fiber comprises a plurality of swelling or contracting polymer stripes embedded in a corresponding plurality of semicircular notches defined into a polymer coating on the exterior of the cladding of the optic fiber to induce a corresponding plurality of bends in the optic fiber on exposure to the analyte.

8. An apparatus for analyzing an analyte dispersed in a medium comprising:
   an optic fiber with at least one analyte-sensitive material in the form of a swelling or contracting polymer coating circumferentially surrounding the optic fiber, which coating is distributed as a longitudinal sequence of active circumferential stripes along entire length of the optic fiber to create a distributed stress-induced grating in the optic fiber, the analyte-sensitive material inducing a stress on the optic fiber; and
   means for sensing the stress induced on the optic fiber to identify exposure of the analyte-sensitive material to the analyte,
   where the swelling or contracting polymer coating on the exterior of a conventional optic fiber comprises a sequence of periodic longitudinal depositions of the swelling or contracting polymer embedded in a non-sensing polymer coating surrounding the fiber to create a periodic stress-induced grating in the optic fiber.

9. The apparatus of claim 8 where the means for sensing the stress induced on the optic fiber by the sequence of periodic longitudinal depositions of the swelling or contracting polymer embedded in the non-sensing polymer coating surrounding the fiber comprises means for sensing attenuation of light at a predetermined wavelength in the periodic stress-induced grating in the optic fiber.

10. An optic fiber comprising:
   a fiber core;
   cladding;
   a uniform coating of a nonsensing polymer disposed on or in the cladding;
   a sequence of semicircular notches defined in the uniform coatings; and
   sensing swelling or contracting polymer embedded in the semicircular notches.

11. An optic fiber comprising:
   a fiber core;
   cladding;
   a sequence of swelling or contracting rings of polymer, each separated by nonswelling or noncontracting rings of polymer, both being disposed as a coating on the cladding so that a stress-induce optical grating is induced in the core and cladding.

* * * * *

UNITED STATES PATENT AND TRADEMARK OFFICE
CERTIFICATE OF CORRECTION

PATENT NO. : 7,651,862 B2 Page 1 of 1
APPLICATION NO. : 10/469216
DATED : January 26, 2010
INVENTOR(S) : Ponce et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1331 days.

Signed and Sealed this

Twenty-third Day of November, 2010

David J. Kappos
*Director of the United States Patent and Trademark Office*